United States Patent
Titlebaum et al.

(10) Patent No.: US 10,136,963 B2
(45) Date of Patent: Nov. 27, 2018

(54) SYSTEM AND METHOD FOR INTRODUCING PHOTOSENSITIVE DYES VIA AN INSERT INTO A ROOT CANAL IN A TOOTH, METHOD FOR PRODUCING SAID DYE IMPREGNATED INSERT AND METHOD OF USING SAID DYE-IMPREGNATED INSERT

(71) Applicants: Richard Titlebaum, Merion, PA (US); Som Tyagi, Garnet Valley, PA (US)

(72) Inventors: Richard Titlebaum, Merion, PA (US); Som Tyagi, Garnet Valley, PA (US)

(*) Notice: Subject to any disclaimer, the term of this patent is extended or adjusted under 35 U.S.C. 154(b) by 0 days.

(21) Appl. No.: 15/538,227

(22) PCT Filed: Dec. 21, 2015

(86) PCT No.: PCT/US2015/066985
§ 371 (c)(1),
(2) Date: Jun. 21, 2017

(87) PCT Pub. No.: WO2016/106173
PCT Pub. Date: Jun. 30, 2016

(65) Prior Publication Data
US 2018/0000559 A1    Jan. 4, 2018

Related U.S. Application Data

(60) Provisional application No. 62/095,168, filed on Dec. 22, 2014.

(51) Int. Cl.
*A61C 5/50*    (2017.01)
*A61C 19/06*    (2006.01)
(Continued)

(52) U.S. Cl.
CPC ............... *A61C 5/50* (2017.02); *A61C 19/06* (2013.01); *A61K 6/0035* (2013.01); *A61N 5/062* (2013.01);
(Continued)

(58) Field of Classification Search
CPC .. A61C 5/04; A61C 5/50; A61C 19/06; A61C 2201/002; A61K 6/0035; A61N 5/062; A61N 2205/0606
See application file for complete search history.

(56) References Cited

U.S. PATENT DOCUMENTS 7,306,459 B1    12/2007  Williams
8,215,960 B2 *  7/2012   Wagner ................... A61C 5/40
                                                                    433/224

(Continued)

FOREIGN PATENT DOCUMENTS

WO    WO 2009/066294    5/2009

OTHER PUBLICATIONS

International Search Report and Written Opinion for PCT/US15166985, dated Mar. 11, 2016.

(Continued)

*Primary Examiner* — Ralph Lewis
(74) *Attorney, Agent, or Firm* — Joseph E. Maenner; Maenner & Associates, LLC (57)    ABSTRACT

A bactericidal insert for introduction into a canal in a tooth during a root canal procedure is provided, along with a method of producing the insert and a method of using the insert in a root canal procedure. The insert is in the form of a carrier having a plurality of pores or interstices. The carrier had been impregnated with a liquid photosensitive dye so that the dye entered the pores or interstices and then the carrier with the liquid photosensitive dye forms a dye-impregnated carrier. The dye-impregnated carrier is config- (Continued)

ured and adapted for insertion within the canal of the tooth. The carrier, if dried, is adapted to receive a wetting agent to dissolve the dye therein to produce a liquefied dye, which is activatable to produce singlet oxygen within the canal when it is irradiated by light from outside of the tooth.

22 Claims, 6 Drawing Sheets

(51) Int. Cl.
*A61K 6/00* (2006.01)
*A61N 5/06* (2006.01)

(52) U.S. Cl.
CPC *A61C 2201/002* (2013.01); *A61N 2005/0606* (2013.01)

(56) References Cited

U.S. PATENT DOCUMENTS

| | | |
|---|---|---|
| 2004/0053201 A1 | 3/2004 | Dovgan |
| 2004/0199227 A1 | 10/2004 | Altshuler et al. |
| 2008/0070194 A1 | 3/2008 | Wagner et al. |
| 2008/0255498 A1 | 12/2008 | Houle |
| 2012/0264078 A1 | 10/2012 | Patel et al. |

OTHER PUBLICATIONS

International Preliminary Report on Patentability for PCT/US2015/066985, dated Jun. 27, 2017. 9 pages.

* cited by examiner

Plots of photosensitive dye concentration in aqueous solution vs. the free radical concentration for a given time exposure to light (lower curve), and the same plot with increased light flux (upper curve). Light/optical flux being = Intensity x Time. Intensity being = Power/area.

Note: Adding enhancers, e.g., gold or silver nanoparticles, etc., has the same effect as increased light or optical flux.

Fig. 7

Plot of free radical concentration generated vs. irradiation time in a 0.01% aqueous solution of methylene blue. The irradiation source is a red LED ($630\pm10nm$) with an intensity of 500Watts/m².

Fig. 8

Plot of free radical concentration vs. concentration of aqueous solution of methylene blue after an irradiation for 600 sec. The irradiation source is a red LED (630±10nm) with an intensity of 500Watts/m².

SYSTEM AND METHOD FOR INTRODUCING PHOTOSENSITIVE DYES VIA AN INSERT INTO A ROOT CANAL IN A TOOTH, METHOD FOR PRODUCING SAID DYE IMPREGNATED INSERT AND METHOD OF USING SAID DYE-IMPREGNATED INSERT

CROSS-REFERENCE TO RELATED APPLICATIONS

The present application is a 371 of PCT Application PCT/US2015/66985, filed on Dec. 21, 2015, which claims priority from U.S. Provisional Patent Application 62/095,168, filed on Dec. 22, 2014, both of which are incorporated by references in their entireties.

FIELD OF THE INVENTION

This invention relates generally to Dentistry, and more particularly to dye-impregnated inserts for introduction into a canal in a tooth during a root canal procedure for photodynamic therapy, methods of producing such dye-impregnated inserts, and methods of using such dye-impregnated inserts.

BACKGROUND OF THE INVENTION

Endodontic therapy, commonly referred to as a root canal procedure typically involves cleaning out the tooth's pulp from the canal(s) through the tooth's root(s), disinfecting the cleaned out space (canal) and then filling it. It is of utmost importance that all of the bacteria that may have existed in the canal before or during the procedure are eliminated before the canal is filled. See, for example, Hancock H. H. 3rd et al., "Bacteria isolated after unsuccessful endodontic treatment in a North American population", Oral Surgery, Oral Medicine, Oral Pathology, Oral Radiology, Endodontology 2001 May; 91(5):579-86.

Various techniques have been used to disinfect the root canal but all suffer from one or more drawbacks. For example, one technique involves the use of caustic materials, e.g., bleach is one example, as the disinfecting agent introduced into the canal. This presents a risk to the patient if the material leaves the tooth and gets into the jaw or sinus. Other antibacterial techniques can require a substantial amount of time in the dental chair, e.g., five to thirty minutes, and can require multiple visits of anesthesia and drilling of the tooth. As such there is the risk that the patient will not comply and return for follow up to complete the root canal treatment Moreover, at present there are no non-invasive methods to kill bacteria or deal with post-operative flare-ups; a critical concentration of viable bacteria may remain. In fact, if there are post-operative flare-ups or any post-operative failure, currently requires retreatment, surgery or extraction. Further still, at present there is no way for a subsequent Dental professional to identify the particular antibacterial technique that was utilized by the prior Dental professional in carrying out the root canal procedure since, even if records from treating Dental professional exist, many Dental professionals do not keep a detailed record of time of exposure to antibacterial material or the concentration of the antibacterial material used.

Photodynamic therapy (PDT) has been used on a limited basis as a means for killing bacteria within a tooth canal during a root canal procedure. That technique entails flooding the affected tooth with photodynamic or photosensitive dye so that the dye enters into the tooth canal. Then a fiber optic cable is introduced into the canal to irradiate the photosensitive dye with light from within the canal to activate the dye to release free radicals, such as singlet oxygen, which is known to have an anti-microbial or anti-bacterial effect. See, Mohammad Asnaashari et al., "A Comparison of the antibacterial activity of the two methods of photodynamic therapy (using diode laser 810 nm and LED lamp 630 nm) against *Enterococcus Faecalis* in extracted human anterior teeth", Photodiagnosis and Photodynamic Therapy August 2015, A. Rios et al., "Evaluation of photodynamic therapy using a light-emitting diode lamp against *Enterococcus faecalis* in extracted human teeth", Journal of Endodontics 2011 June; 37(6):856-9, and Vaziri S. et al., "Comparison of the bactericidal efficacy of photodynamic therapy, 2.5% sodium hypochlorite, and 2% chlorhexidine against *Enterococcous faecalis* in root canals; an in vitro study", Dental Research Journal 2012 September; 9(5):613-8.

While such a photodynamic technique appears to present some advantages over other antibacterial techniques, such technique still leaves much to be desired from various standpoints. For example, the amount of light delivered into the tooth canal to activate the photosensitive dye is limited to the size of the optic fiber. Furthermore, light from the optical fiber may not reach crevices that are not in the direct path of the incident light. Moreover, the flooding of the tooth with the liquid dye is messy since the liquid dye stains the teeth and gums. Moreover, that liquid dye may not gain complete access into the full depth of the tooth canal. Further yet, viable bacteria may remain present in the root canal, leaving the potential for reinfection at some point in the future. Further still, the entire procedure has to be accomplished within the Dentist's office, with the tooth canal still being exposed to allow entry of the fiber-optic cable. The above prior art methods do not permit treatment of the tooth canal once the tooth canal has been sealed.

Accordingly, a need exists for a better photodynamic root canal procedure which overcomes the disadvantages of the prior art and also provides a viable and effective means for carrying it out. The subject invention addresses those needs.

SUMMARY OF THE INVENTION

In accordance with one aspect of this invention there is provided a bactericidal insert for introduction into a canal in a tooth during a root canal procedure. The insert comprises a carrier having a plurality of pores or interstices having been impregnated with a liquid photosensitive dye so that the dye enters the pores or interstices and then the carrier with the liquid photosensitive dye forms a dye-impregnated carrier which may remain wet or be dried. The dye-impregnated carrier is configured for insertion within the canal of the tooth, and if dried it is also configured to be wetted to dissolve the dye to produce a liquefied dye. The liquefied dye is activatable to produce irradiated by light from outside of the tooth.

Another aspect of this invention entails a method of producing a bactericidal insert for introduction into a canal in a tooth during a root canal procedure. The method basically comprises providing a carrier having a plurality of pores or interstices. The carrier had been impregnated with a liquid photosensitive dye so that the dye enters the pores or interstices of the carrier to form a dye-impregnated carrier. The dye-impregnated carrier is arranged to be wetted by a wetting agent to produce a liquefied photosensitive dye therefrom. The liquefied photosensitive dye is activatable to produce singlet oxygen when irradiated by light from outside of the tooth.

Still another aspect of this invention entails a method of killing bacteria in a canal in a tooth during a root canal procedure. The method basically comprises providing a dry dye-impregnated carrier having a plurality of pores or interstices. The carrier had been impregnated with a liquid photosensitive dye so that the dye entered the pores or interstices to form the dye-impregnated carrier. In accordance with one aspect of that method if the carrier was dried, the dry dye-impregnated carrier is introduced into the canal in the tooth to a desired position and then wetted therein, e.g., via the natural moisture within the tooth canal or by a wetting agent introduced into the canal, to produce a liquefied photosensitive dye.

Thereafter the tooth is irradiated, at a time to be determined by the Dentist and/or the patient, with light from outside the tooth to activate the liquefied photosensitive dye within the canal, whereupon the liquid photosensitive dye produces singlet oxygen to act as a bactericide in the canal of the tooth to kill the bacteria therein. At another time to be determined by the Dentist and/or the patient, the tooth may be re-irradiated.

In accordance with another aspect of the foregoing method the dry dye-impregnated carrier is wetted prior to introduction into the canal of the tooth, e.g., the carrier is wetted with a wetting agent to produce the liquefied photosensitive dye, and that rewetted carrier is introduced into the canal of the tooth. The tooth is then irradiated with light from outside the tooth to activate the liquefied photosensitive dye within the canal, whereupon the liquid photosensitive dye produces singlet oxygen to act as a bactericide in the canal of the tooth to kill the bacteria therein.

This invention is not limited to root canal procedures. In this regard in accordance with another aspect of this invention a bactericidal component for application on (e.g., as a bandage for a wound), or in (e.g., as a packing for periodontal pocket) the body of a patient is provided. That component comprises a carrier having a plurality of pores or interstices having been impregnated with a liquid photosensitive dye so that the dye enters said pores or interstices and then the carrier with the liquid photosensitive dye therein having been dried to form a dye-impregnated carrier. The dye-impregnated carrier is configured for application to or insertion in the body of a patient and also configured to be wetted to liquefy the dye to produce a liquefied dye. The liquefied dye is activatable to produce singlet oxygen when irradiated by light.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements. In the drawings:

DETAILED DESCRIPTION OF THE PRESENT INVENTION

Figure 1:
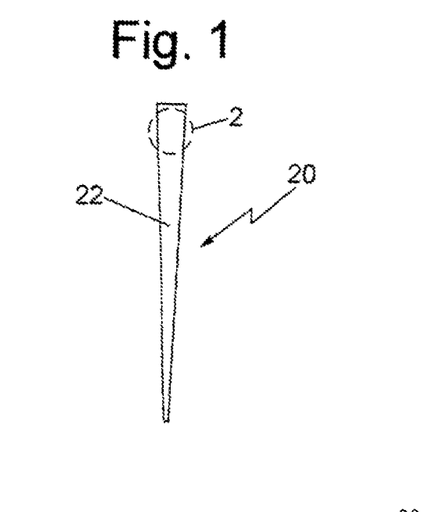
FIG. 1 is an enlarged side elevation view of one exemplary bactericidal insert, e.g., a paper point, constructed in accordance with this invention for introduction into a canal in a tooth during a root canal procedure.
Figure 2:
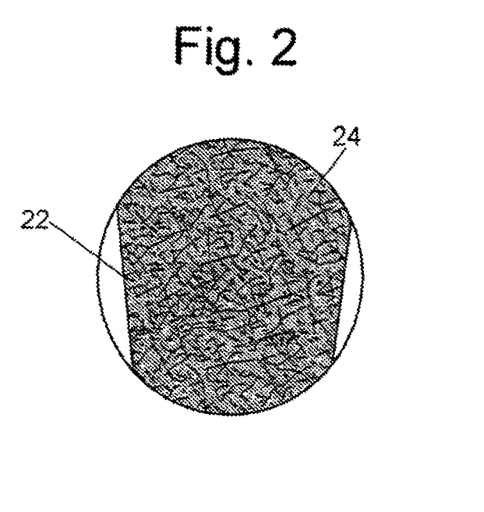
FIG. 2 is an enlarged view of the portion of the insert of FIG. 1 shown within the circle identified by the reference number 2.
Figure 3:
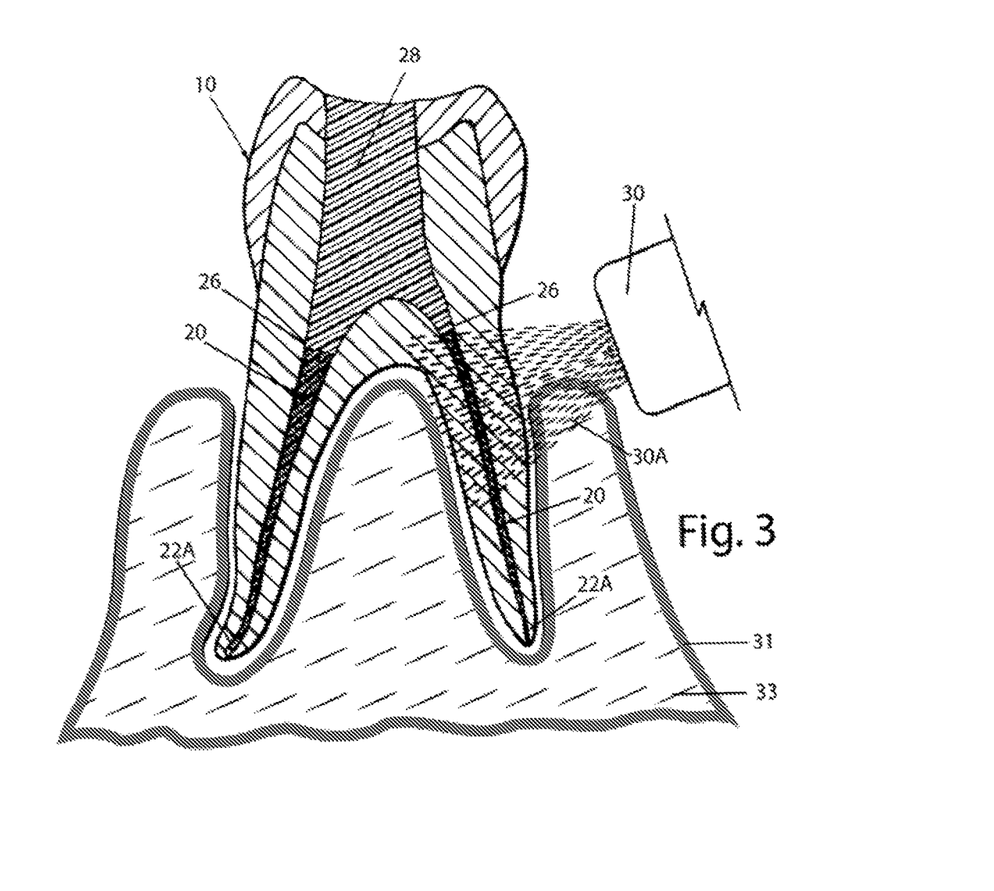
FIG. 3 is a greatly enlarged illustration of a tooth, with its surrounding gum structure and bone structure, but shown in cross-section into which inserts like shown in FIG. 1 have been inserted into two prepared canals within the tooth, and showing the irradiation of the inserts via light applied from outside the tooth.

Referring now to the various figures of the drawing wherein like reference characters refer to like parts, there is shown at 20 in FIGS. 1 and 2 one exemplary embodiment of a bactericidal insert for introduction into a canal in a tooth 10 during a root canal procedure. The insert 20 basically comprises a carrier 22 which is porous and includes a photosensitive dye 24, (to be described later) which had been introduced into its pores or interstitial spaces and maintains its wet state or, optionally, is then dried. The insert is arranged to be deployed within the prepared canal 26 (FIG. 3) in the tooth with the photosensitive dye, if having been optionally dried, then wetted to produce a liquefied photosensitive dye, which is then activated by a light source external to the tooth to generate and release singlet oxygen into the canal to destroy any bacteria therein. In the embodiment shown the tooth has two roots so each root has an insert constructed in accordance with this invention deployed therein. It should be noted at this juncture that the location of the top end portion of each of the inserts 20 shown in FIG. 3 is for illustrative purposes only and may not represent the actual location in a particular patient's tooth.

As best seen in FIG. 1 in accordance with one exemplary preferred embodiment the carrier is in the form of a conventional "paper point", like that used in traditional endodontic procedures and which is available from various manufacturers/suppliers. The carrier may take forms other than simple paper points, such as paper points with a solid metal core or metal impregnated in the paper, engineered points with nano-porous cavities made of gutta percha or some other material, nano-porous ceramic materials, sponges, etc., so long as the carrier is of a shape and construction which is capable of being inserted into a prepared canal 26 in a tooth and to extend sufficiently deeply within the canal so that the singlet oxygen released by its photosensitive dye can reach all portions of the canal. In this regard, preferably, the material of the carrier should be somewhat resistant to compression and deformation as the carrier is introduced into the canal to ensure that the carrier can reach the lowermost portions of the canal. Moreover, the carrier can be designed so that its pores or interstitial spaces are of a desired size to effectively hold the photosensitive dye therein.

Figure 4:
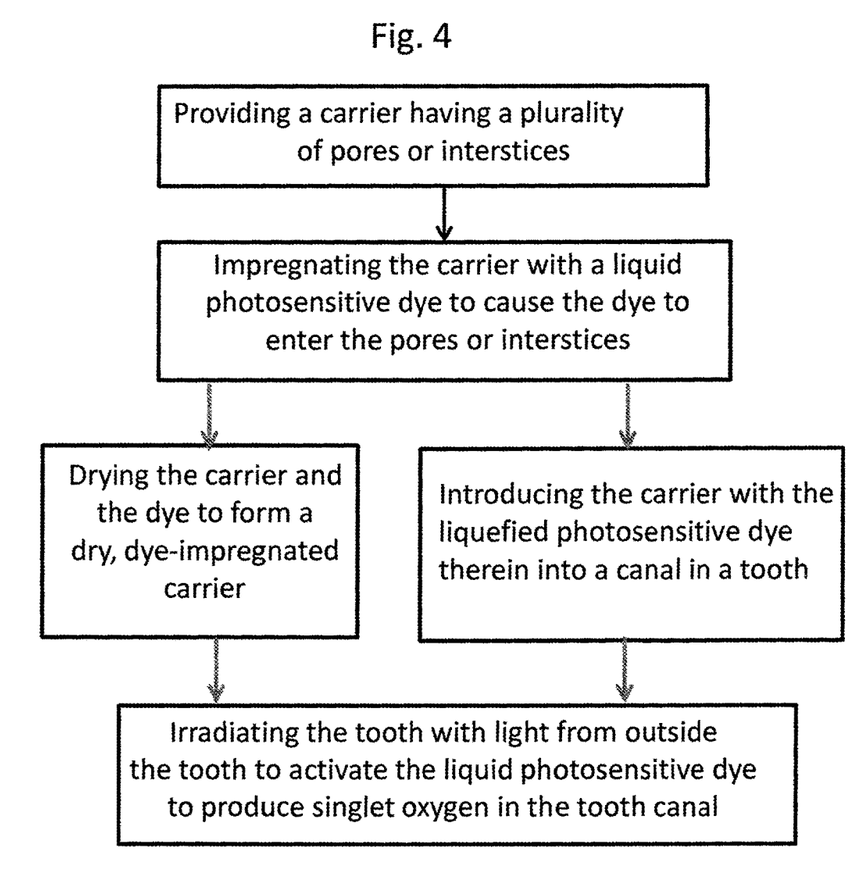
FIG. 4 is a block diagram showing one method in accordance with this invention for producing bactericidal inserts of this invention.

In accordance with one aspect of this invention and as shown in the flowchart of FIG. 4 the porous inserts 22 can be prepared by soaking them in the photosensitive dye 24. The dye-soaked inserts 20 may be washed to remove excess dye. The washing, if used, will leave a sufficient amount of the dye within the pores, and within the fibers of the paper point carrier, to be activated by the light to produce the singlet oxygen, if the carrier is subsequently wetted and thereafter irradiated with light, as will be described later.

Still alternatively, instead of drying the carrier and the dye 24, the dye 24 may remain liquefied within the carrier for introduction of the carrier with the liquefied dye into the tooth canal 26 and then sealed into the tooth 10. The tooth 10 can be subsequently irradiated to activate the liquefied dye 24 to produce singlet oxygen in the tooth canal 26.

The carrier with the photosensitive dye therein, whether wet or dry, has sufficient resistance to axial compression so that the carrier can be deployed or introduced into the canal by inserting its pointed distal end 22A into the prepared tooth canal 26 and then tamped or otherwise pressed down the canal until its distal end reaches the bottom of the canal or as close to it as necessary. Once the insert 20 is in position, if dry, insert 20 can be wetted with any suitable wetting agent, e.g., a few drops of water or saline or an antibacterial solution, or wetting by the naturally occurring moisture in the tooth, whereupon the wetting agent/natural tooth moisture wicks down the length of the insert to release or re-liquefy the dried photosensitive dye. The liquid photosensitive dye can then diffuse into the surrounding tooth structure.

The inserts can then be sealed within the tooth with any suitable conventional filling 28, thereby sealing the inserts with the now liquid photosensitive dye within the tooth's canals. The tooth can then be exposed to suitable activating light 30A from outside of the tooth by a suitable light source 30 to activate the dye 24 (which is not only resident in the canal but has also diffused into the surrounding tooth structure), whereupon the dye 24 releases singlet oxygen thereby killing any bacteria to which the dye 24 is exposed. Moreover, since the liquid photosensitive dye will diffuse with time from the canal, the subject invention enables killing bacteria in a wider area than the area to which the photosensitive dye was initially delivered. Further still, since the insert is totally sealed within the tooth, staining of the adjacent teeth and gums does not result.

As shown in FIG. 3, activating light 30A can be shone directly on tooth 10, allowing the light to pass through tooth 10 and to insert 20 to activate the photosensitive dye within insert 20. Alternatively, activating light 30A can be shown on gum 31, passing through gum 31 and bone 33, as well as tooth 10 to insert 20 to activate the photosensitive dye within insert 20.

Figure 3A:
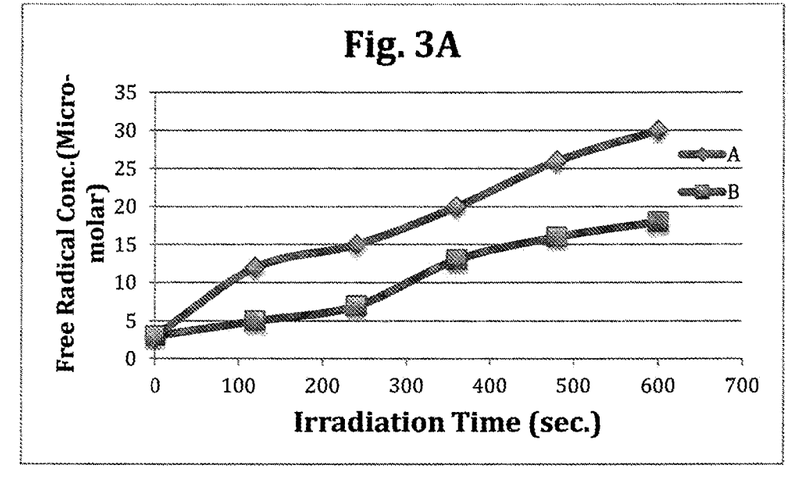
FIG. 3A is a plot of free radical concentration generated vs. irradiation time in a porous insert of FIG. 1 soaked with a 0.01% aqueous solution of methylene blue.

FIG. 3A is a plot of free radical concentration generated vs. irradiation time in a porous insert 22 of FIG. 1 soaked with a 0.01% aqueous solution of methylene blue and placed: [A] inside a tooth as shown in FIG. 3, and [B] placed on the inner surface of a pig's jaw, such that the light is incident on the outer surface of pig's jaw and transmitted through gum, bone and tooth tissues. In both cases, the irradiation source is a red LED (630±10 nm) with an intensity of 500 Watts/m$^2$. While plot A shows a higher free radical concentration, plot B shows that application of an activating light against a gum/jawbone still transmits sufficient irradiation energy there through to generate a high free radical concentration for effective treatment. In fact by 600 seconds, light transmitted through bone 33, gum 31, and tooth 10 (plot B), which is more distance than light will have to travel through in a patient, caused more free radical generation than when light passed solely through the extracted tooth (plot A) at 300 seconds.

It should be pointed out at this juncture that the means for irradiating the tooth with the activating light can be provided by any suitable means 30. For example such means could comprise a small hand holdable illumination device, such as an LED laser, that is arranged to be inserted into the patient's mouth closely adjacent the tooth in issue. The patient himself/herself can hold that illumination device while in the dental chair to activate the photosensitive dye, thereby freeing the Dentist for other activities. In fact, it is contemplated that the patient may be provided with an illumination device to take home to use at some subsequent time to reactivate the photosensitive dye within the tooth and thereby kill any bacteria that may have avoided destruction upon the first application of the light therapy. Such application of the illumination device may be performed multiple, or virtually unlimited, times to reactivate the photosensitive dye each time that the illumination device is applied.

While the light source for activating the photosensitive dye of the insert has been described above as being a hand-held device, such as could be used by the patient, it could also be designed to adhere to gum tissue as a cover or sit on gum tissue or be designed as a modified cotton roll or other gauze, with a built-in light and power source.

In whatever form the light is manufactured, the light could also include some control circuitry to establish a preset amount of time and the times that the light operates so that patient compliance is unnecessary. The light could also be manufactured to keep a record of the amount of time that the light was turned on to corroborate reported patient compliance. In accordance with one preferred exemplary embodiment of the invention the photosensitive dye is selected from the group consisting of Gentian Violet, Crystal Violet, Toluidine Blue, Indocyanine Green, Xanthines (e.g., Rose Bengal, Fluorescein, Eosin, Erythrosine, etc.) Phenothiazines (e.g., Methylene Blue), Porphyrins, etc. Those dyes when in liquid form and irradiated by light of an appropriate wavelength, e.g., a wavelength near the maximum absorption of the dye being used, produce free radicals. In particular, usually singlet oxygen is produced, but other free radical species have been reported. Those free radicals have a deleterious effect on bacterial cells. While the host cells may also subject to the deleterious effects of the free radicals, it appears that the amount of free radicals necessary to destroy the bacterial cells is lower than the amount that would cause appreciable harm to host cells. Moreover, the photosensitive dye and light combination as delivered by this invention is effectively targeted since the dye and light combination is delivered in a confined location, namely, within the tooth canal and thus does not have to be delivered systemically.

In lieu of, or in addition to, the photosensitive dyes described above, other dyes, such as, for example, annatto extract, anthocyanins, B-carotene, beta APO 8 Carotenal, black currant, burnt sugar, Canthaxanthin, caramel, carbo medicinalis, carmine, carmine blue, carminic acid, carrot, chlorophyll, chlorophyllin, cochineal extract, copper chlorophyll, copper chlorophyllin, curcumin, curcumin/CUchloro, grape, hibiscus, lutein, mixed carotenoids, paprika, riboflavin, spinach, stinging nettle, titanium dioxide, turmeric, aronia/red fruit, beet juice, paprika extract, paprika oleoresin, amaranth, black PN, carmoisine, fast red E, erythrosine, green S, patent blue V, ponceau 4R, quinoline yellow, Red 2G, sunset yellow, tartrazine, Lake allura red, Lake amaranth, Lake brilliant blue FCF, Lake carmosine, Lake erythrosine, Lake indigo carmine, Lake ponceau 4R, Lake quinoline yellow, Lake sunset yellow, Tartrazine (FD&C Yellow No. 5) Curcumin, Riboflavin 5'-monophosphate sodium salt 441, Allura Red AC (FD&C Red No. 40) New Coccine (CI 16255, Food Red 7), Chromotrope FB (CI 14720, Food Red 3), Indigo Carmine (FD&C Blue No. 1), FD&C blue #2, Lissamine Green B Napthol Green or Acid Green Cochineal 530, Carmoisine azorubine 515, Amaranth 523, Brillant Scarlet 4R 503, Chlorophylls and copper complexes 633, Brillant black BN (PN), Chocolate Brown HT, Beta-carotene 470, Bixin Lycopene 530, Betanin Riboflavin 445, Riboflavin 5I-monophosphate sodium salt 441, Erythrosin B sodium salt, teas, and/or juices, can also be applied to the subject tooth to generate free radicals.

If desired, the insert may include a radio-opaque material or tag. For example, the insert with its tagged porous/nanoporous material and photoactive dye would be sealed in place and the tooth can be restored on top of the insert. This would be much faster and less technically challenging than current or past techniques. Moreover, the insert with the radio-opaque tag could be readily identified by radiograph to verify its presence and to provide an indication of the type of antibacterial treatment that was performed. With current technologies, one can determine by x-ray or other examination that a root canal treatment has been completed, but one would have absolutely no idea what protocol, if any, was used to attempt to kill the bacteria in the tooth during the procedure.

Figure 5:
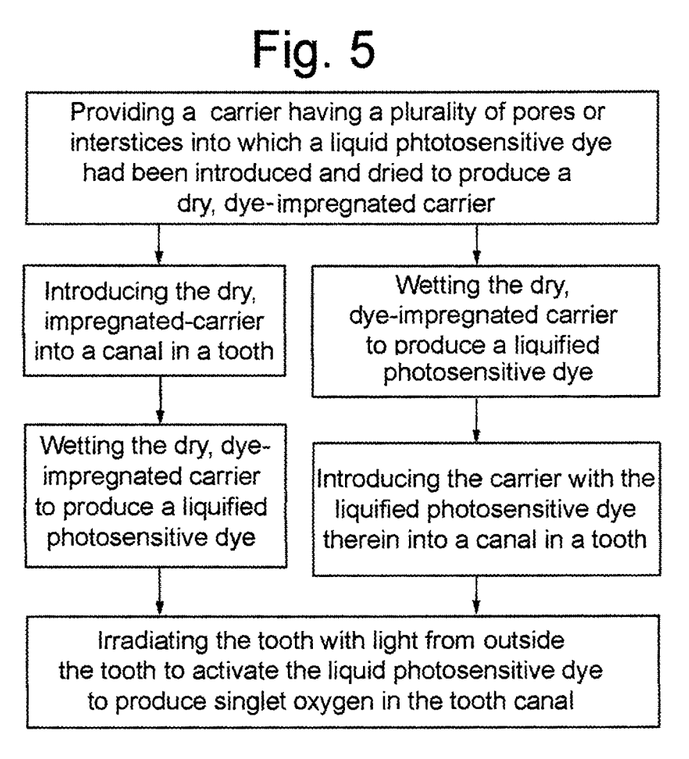
FIG. 5 is a block diagram showing two methods in accordance with this invention for killing bacteria within a canal in a tooth using an insert constructed in accordance with this invention.

Turning now to FIG. 5 the details of two methods of destroying bacteria in a root canal will now be described. One method shown by the sequence of events on the left side of the flow diagram basically comprises providing a dry dye-impregnated carrier having a plurality of pores or interstices which carrier had been impregnated with a liquid photosensitive dye so that the dye entered the pores or interstices. The carrier with the liquid photosensitive dye therein had been dried to form the dry dye-impregnated carrier.

The dry dye-impregnated carrier is introduced into the canal in the tooth to a desired position. When said dry, dye-impregnated carrier is in that desired position a portion thereof is located adjacent the surface of the tooth contiguous with the canal. The dry dye-impregnated carrier is then wetted by either the use of a wetting agent or by the natural moisture within the tooth canal, whereupon said moisture/wetting agent wicks through the dry dye-impregnated carrier to produce liquefied photosensitive dye and the insert is then sealed within the tooth by any conventional sealing technique. After that has been accomplished the tooth is irradiated with light from outside the tooth to activate the liquefied photosensitive dye within the canal, whereupon the liquid photosensitive dye produces singlet oxygen to act as a bactericide in the canal of the tooth to kill the bacteria therein.

As an alternative to the method described immediately above for destroying bacteria in a root canal procedure, and as shown by the sequence of events shown on the right side of the flow diagram the dry dye-impregnated carrier is wetted prior to introduction into the canal of the tooth, e.g., the carrier is wetted with a wetting agent to produce the liquefied photosensitive dye, and that rewetted carrier is introduced into the canal of the tooth. The insert with the wetted carrier may be provided in a sealed package, which can be opened when needed and the wetted insert removed from the package and then introduced into the prepared canal.

Alternatively, the insert can be provided in a dry state and then wetted prior to deployment into the prepared canal. In any case, once the wetted insert is within the canal and is sealed therein, such as described above, the tooth can then irradiated with light from outside the tooth to activate the liquefied photosensitive dye within the canal, whereupon the liquid photosensitive dye produces singlet oxygen to act as a bactericide in the canal of the tooth to kill the bacteria therein.

Figure 6:
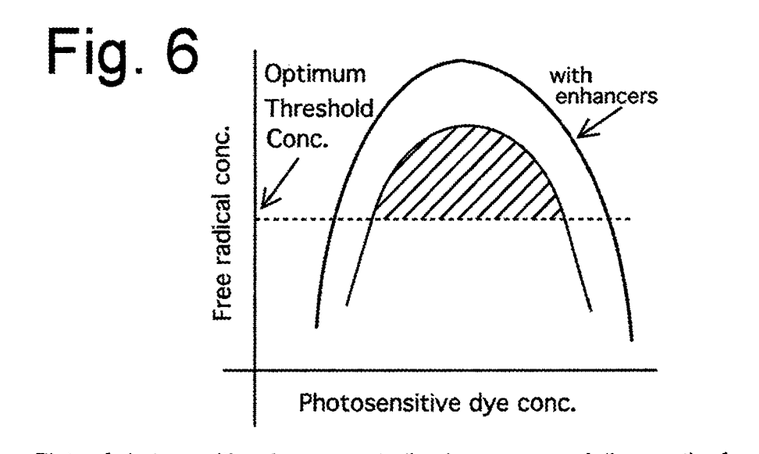
FIGS. 6-8 constitute charts of tests conducted using components of the subject invention.
Figure 7:
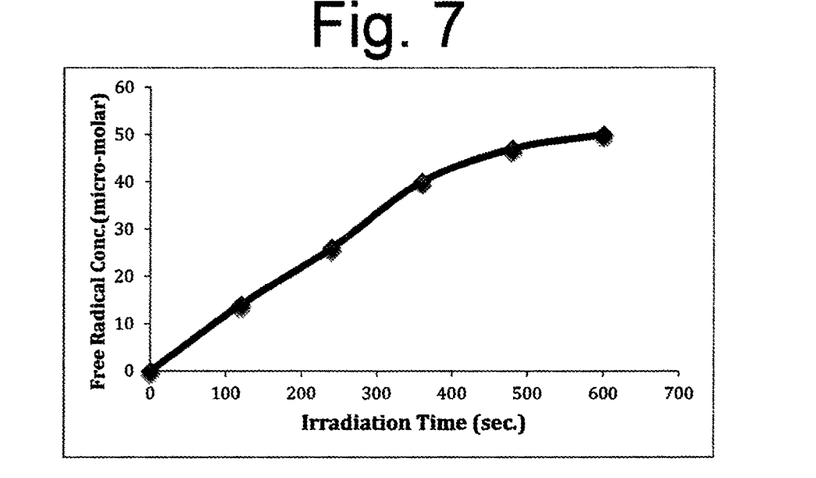
Figure 8:
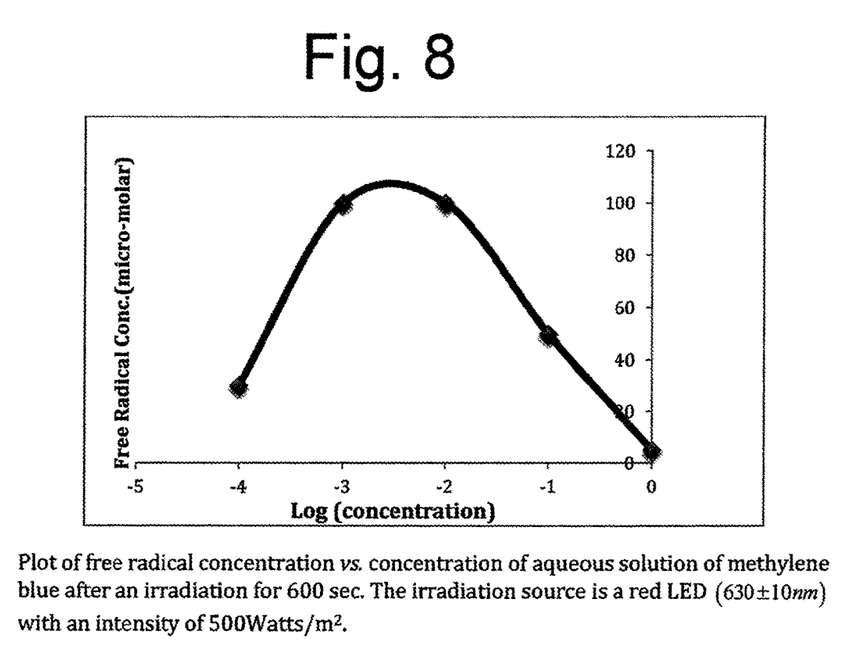

It should be pointed out at the juncture that the inventors have carried out some preliminary in vitro tests of carriers and some photo sensitive dyes like those used in the subject invention. The charts shown in FIGS. 6-8 represent some preliminary findings indicating the efficacy of the release of free radicals, e.g., singlet oxygen, when subjected to suitable light for activating the photosensitive dyes.

As should be appreciated by those skilled in the art from the foregoing the subject invention provides a viable means for ensuring that all bacteria are killed by a root canal procedure making use of an insert and methods in accordance with this invention. Even if all bacteria are not killed by the initial application of light, with the insert remaining sealed within the tooth's canal additional exposures to light from outside the tooth can be accomplished thereafter to effectively destroy any residual bacteria.

Moreover, the subject invention can decrease "chair time" for the Dentist as the activating light can be delivered without the patient being in the chair. In fact the activating light can be delivered outside of the Dentist's office. The activating light can be delivered for an extended period of time and can be reapplied by the patient if there is pain or swelling during post-operative period or if infection recurs at some future time. In this regard if bacteria or infection persist or return at some point after treatment, the subject invention provides the ability for the patient to have the tooth irradiated again, non-invasively, and potentially killing any residual bacteria at this later date. Additionally, the activating light can be periodically repeatedly applied to the tooth, such as, for example, during semiannual dental check-ups, thereby reactivating the dye during each repeated light application. It should be emphasized that the creation of the singlet oxygen species by photo-excitation is a completely reversible phenomenon. This means that the efficacy of the dye to produce singlet oxygen species does not diminish with repeated photo-excitation.

It should be appreciated also that the activating light does not necessarily have to be delivered at the time of insertion of the dye-impregnated carrier into the tooth canal, but instead, can be delivered at a later date, and at a location outside the Dentist's office, such as, for example, by self radiating by the patient in the patient's home.

Currently the only methods to deal with recurrent infection are invasive and involve either redoing the root canal treatment, a surgical treatment of the root and the surrounding infection, or an extraction. The subject invention should spare the patient these invasive treatments.

The following table represents the advantages of the PDT treatment in root canal procedures as provided by the subject invention over prior art PDT treatments.

| Prior Art PDT Invention | PDT of the subject |
|---|---|
| Liquid | Porous/nanoporous with material dye incorporated |
| Entire treatment in Dental office, taking up patient and the Dentist's time | Once sealed in tooth, no Dental office time needed |
| Photon flux limited by the size of fiber cross-section. Only those regions that are in the direct path of the incident light can be treated | Much higher photon flux can be utilized. All regions in the tooth can be illuminated. |

-continued

| Prior Art PDT Invention | PDT of the subject |
|---|---|
| Invasive for repeat treatment | Non-invasive for repeat treatment |
| No thought about | Ideal concentration determined |
| Narrow spectrum of light | Wide spectrum of light |
| Light into canal | Light from outside with either a hand held light source or a device that is attached to or placed near gum and tooth |

Accordingly, the subject invention provides a means and method to disinfect a root canal with the potential for future disinfection that can replace current filling materials/techniques used in root canal procedures. Moreover, if necessary to retreat or re-enter the root canal space, the insert of this invention could be removed easier and faster than anything that is currently used. Further still, if desired the carrier may contain photosensitive dye and any type of enhancer, such as but not limited to, ethylenediaminetetraacetic acid (EDTA), nanoparticles of gold or silver, quantum dots, graphene, sodium ascorbate, etc.

It must be noted at this time that the subject invention can be used for other dental applications than root canal procedures. For example, a photosensitive dye, like those described above, can be incorporated into a carrier that can be packed into a periodontal pocket, then activated with an external light. The carrier can be removed at a later date after periodontal pocket has been sufficiently disinfected/sterilized. Alternatively, the carrier can be designed to absorb over time.

In fact, the subject invention is not limited to dental applications. In this regard, the subject invention may be used as a means of wound protection or wound therapy. For example, an enhanced antibacterial bandage can be constructed in accordance with this invention having a carrier, e.g., a porous gauze, holding the photosensitive dye and which can be activated with an external light to decrease wound healing time, prevent Methicillin-resistant *Staphylococcus aureus* (MRSA) and other infections, prevent cross-infection, provide skin disinfection prior to surgery. Such devices could decrease post-operative infection and reduce hospital readmissions, decrease mortality, decrease cost to the patient, the hospital and the insurance company. Such a device could also provide post-surgical wound protection and suture site protection. It is contemplated that those bandages may also be designed with light built into the gauze and with its own power supply so that patient compliance is unnecessary.

Without further elaboration the foregoing will so fully illustrate our invention that others may, by applying current or future knowledge, adopt the same for use under various conditions of service.

We claim:

1. A bactericidal insert for introduction into a canal in a tooth during a root canal procedure, said insert comprising a carrier having a plurality of pores or interstices having been impregnated with a liquid photosensitive dye so that said dye enters said pores or interstices and then said carrier with said liquid photosensitive dye forms a dye-impregnated carrier, said dye-impregnated carrier being configured for insertion within the canal of the tooth and also, the dye can be wet or dried and, if dried, configured to be wetted to dissolve said dye to produce a liquefied dye, said liquefied dye being activatable to produce singlet oxygen or free radicals within said canal when irradiated by light from outside of the tooth;
  wherein said insert is configured so that a wetting agent can be added thereto to wet said dry dye-impregnated carrier and wherein said insert is packaged in a package with said wetting agent.

2. The bactericidal insert of claim 1 wherein said carrier is formed of paper.

3. The bactericidal insert of claim 1 wherein said dye is selected from the group consisting of Gentian Violet, Crystal Violet, Toluidine Blue, Indocyanine Green, Xanthines such as Rose Bengal, Fluorescein, Eosin, Erythrosine, Phenothiazines such as Methylene Blue, Porphyrins, annatto extract, anthocyanins, B-carotene, beta APO 8 Carotenal, black currant, burnt sugar, Canthaxanthin, caramel, carbo medicinalis, carmine, carmine blue, carminic acid, carrot, chlorophyll, chlorophyllin, cochineal extract, copper chlorophyll, copper chlorophyllin, curcumin, curcumin/CU-chloro, grape, hibiscus, lutein, mixed carotenoids, paprika, riboflavin, spinach, stinging nettle, titanium dioxide, turmeric, aronia/red fruit, beet juice, paprika extract, paprika oleoresin, amaranth, black PN, carmoisine, fast red E, erythrosine, green S, patent blue V, ponceau 4R, quinoline yellow, Red 2G, sunset yellow, tartrazine, Lake allura red, Lake amaranth, Lake brilliant blue FCF, Lake carmosine, Lake erythrosine, Lake indigo carmine, Lake ponceau 4R, Lake quinoline yellow, Lake sunset yellow, Tartrazine (FD&C Yellow No. 5) Curcumin, Riboflavin 5'-monophosphate sodium salt 441, Allura Red AC (FD&C Red No. 40) New Coccine (CI 16255, Food Red 7), Chromotrope FB (CI 14720, Food Red 3), Indigo Carmine (FD&C Blue No. 1), FD&C blue #2, Lissamine Green B Napthol Green or Acid Green Cochineal 530, Carmoisine azorubine 515, Amaranth 523, Brillant Scarlet 4R 503, Chlorophylls and copper complexes 633, Brillant black BN (PN), Chocolate Brown HT, Beta-carotene 470, Bixin Lycopene 530, Betanin Riboflavin 445, Riboflavin 5I-monophosphate sodium salt 441, Erythrosin B sodium salt, and teas.

4. The bactericidal insert of claim 1 additionally comprising an enhancing agent to enhance the production of singlet oxygen or free radicals within said canal.

5. The bactericidal insert of claim 4 wherein said enhancing agent is selected from the group consisting of EDTA, gold nanoparticles, silver nanoparticles, quantum dots, graphene and sodium ascorbate.

6. The bactericidal insert of claim 1 wherein said insert is configured so that the natural moisture within the tooth canal wets said dry dye-impregnated carrier.

7. The bactericidal insert of claim 1, wherein said dye remains liquefied within the carrier without being dried.

8. The bactericidal insert of claim 1, wherein the insert is radio-opaque.

9. A method of producing a bactericidal insert for introduction into a canal in a tooth during a root canal procedure, said method comprising:
  a) providing a carrier having a plurality of pores or interstices;
  b) impregnating said carrier with a liquid photosensitive dye so that said dye enters said pores or interstices; and
  c) drying said carrier and said dye to form a dry dye-impregnated carrier, said dry impregnated carrier being arranged to be wetted by a wetting agent to produce a liquefied photosensitive dye therefrom, said liquefied photosensitive dye being activatable to produce free radicals when irradiated by light from outside the tooth, wherein said insert is configured so that a wetting agent can be added thereto to wet said dry dye-impregnated carrier and wherein said insert is packaged in a package with said wetting agent.

10. The method of claim 9 wherein said insert is configured so that the natural moisture within the tooth canal wets said dry dye-impregnated carrier.

11. The method of claim 9 wherein said carrier is formed of paper.

12. The method of claim 9 wherein said dye is selected from the group consisting group consisting of Gentian Violet, Crystal Violet, Toluidine Blue, Indocyanine Green, Xanthines, Rose Bengal, Fluorescein, Eosin, Erythrosine, Phenothiazines, Methylene Blue, and Porphyrins, annatto extract, anthocyanins, B-carotene, beta APO 8 Carotenal, black currant, burnt sugar, Canthaxanthin, caramel, carbo medicinalis, carmine, carmine blue, carminic acid, carrot, chlorophyll, chlorophyllin, cochineal extract, copper chlorophyll, copper chlorophyllin, curcumin, curcumin/CU-chloro, grape, hibiscus, lutein, mixed carotenoids, paprika, riboflavin, spinach, stinging nettle, titanium dioxide, turmeric, aronia/red fruit, beet juice, paprika extract, paprika oleoresin, amaranth, black PN, carmoisine, fast red E, erythrosine, green S, patent blue V, ponceau 4R, quinoline yellow, Red 2G, sunset yellow, tartrazine, Lake allura red, Lake amaranth, Lake brilliant blue FCF, Lake carmosine, Lake erythrosine, Lake indigo carmine, Lake ponceau 4R, Lake quinoline yellow, Lake sunset yellow, Tartrazine (FD&C Yellow No. 5) Curcumin, Riboflavin 5'-monophosphate sodium salt 441, Allura Red AC (FD&C Red No. 40) New Coccine (CI 16255, Food Red 7), Chromotrope FB (CI 14720, Food Red 3), Indigo Carmine (FD&C Blue No. 1), FD&C blue #2, Lissamine Green B Napthol Green or Acid Green Cochineal 530, Carmoisine azorubine 515, Amaranth 523, Brillant Scarlet 4R 503, Chlorophylls and copper complexes 633, Brillant black BN (PN), Chocolate Brown HT, Beta-carotene 470, Bixin Lycopene 530, Betanin Riboflavin 445, Riboflavin 5I-monophosphate sodium salt 441, Erythrosin B sodium salt, and teas.

13. The method of claim 9 wherein said bactericidal insert comprises an enhancing agent to enhance the production of singlet oxygen or free radicals within said canal.

14. The method of claim 13 wherein said enhancing agent is selected from the group consisting of EDTA, metallic nano-particles that are good electrical conductors, such as gold, silver and copper, quantum dots, carbon nanotubes, quantum dots, graphene and sodium ascorbate.

15. A method of killing bacteria in a canal in a tooth during a root canal procedure, said method comprising:
a) providing a dye-impregnated carrier having a plurality of pores or interstices, said carrier having been impregnated with a liquid photosensitive dye so that said dye enters said pores or interstices;
a1) drying the dye;
b) introducing said dry dye-impregnated carrier into the canal in the tooth to a desired position;
b1) wetting said dry dye-impregnated carrier to produce a liquefied photosensitive dye therefrom; and
c) irradiating the tooth with light from outside the tooth to activate said liquefied photosensitive dye, whereupon said liquid photosensitive dye produces singlet oxygen or free radicals to act as a bactericide in the canal of the tooth to kill the bacteria therein.

16. The method of claim 15 wherein when said dry, dye-impregnated carrier is in said desired position a portion thereof is located adjacent the surface of the tooth contiguous with the canal and wherein said wetting of said dry dye-impregnated carrier is achieved by the natural moisture within the tooth canal, whereupon said moisture wicks through said dry dye-impregnated carrier to produce said liquefied photosensitive dye.

17. The method of claim 15 wherein when said dry dye-impregnated carrier is in said desired position a portion thereof is located adjacent the surface of the tooth contiguous with the canal and wherein said wetting of said dry dye-impregnated carrier is achieved by use of a wetting agent introduced into the tooth canal, whereupon said wetting agent wicks through said dry dye-impregnated carrier to produce said liquefied photosensitive dye.

18. The method of claim 15 wherein said wetting of said dry dye-impregnated carrier is accomplished prior to the introduction of said dry dye-impregnated carrier into the canal, whereupon said wetting agent wicks through said dry dye-impregnated carrier to produce said liquefied photosensitive dye.

19. The method of claim 18 wherein said carrier with said liquefied photosensitive dye therein is provided in a package for maintaining the liquidity of said liquefied photosensitive dye.

20. The method of claim 15 wherein said carrier is formed of paper.

21. The method of claim 15 wherein said dye is selected from the group consisting of Gentian Violet, Crystal Violet, Toluidine Blue, Indocyanine Green, Xanthines, Rose Bengal, Fluorescein, Eosin, Erythrosine, Phenothiazines, Methylene Blue, Porphyrins, annatto extract, anthocyanins, B-carotene, beta APO 8 Carotenal, black currant, burnt sugar, Canthaxanthin, caramel, carbo medicinalis, carmine, carmine blue, carminic acid, carrot, chlorophyll, chlorophyllin, cochineal extract, copper chlorophyll, copper chlorophyllin, curcumin, curcumin/CU-chloro, grape, hibiscus, lutein, mixed carotenoids, paprika, riboflavin, spinach, stinging nettle, titanium dioxide, turmeric, aronia/red fruit, beet juice, paprika extract, paprika oleoresin, amaranth, black PN, carmoisine, fast red E, erythrosine, green S, patent blue V, ponceau 4R, quinoline yellow, Red 2G, sunset yellow, tartrazine, Lake allura red, Lake amaranth, Lake brilliant blue FCF, Lake carmosine, Lake erythrosine, Lake indigo carmine, Lake ponceau 4R, Lake quinoline yellow, Lake sunset yellow, Tartrazine (FD&C Yellow No. 5) Curcumin, Riboflavin 5'-monophosphate sodium salt 441, Allura Red AC (FD&C Red No. 40) New Coccine (CI 16255, Food Red 7), Chromotrope FB (CI 14720, Food Red 3), Indigo Carmine (FD&C Blue No. 1) FD&C blue #2, Lissamine Green B Napthol Green or Acid Green Cochineal 530, Carmoisine azorubine 515, Amaranth 523, Brillant Scarlet 4R 503, Chlorophylls and copper complexes 633, Brillant black BN (PN), Chocolate Brown HT, Beta-carotene 470, Bixin Lycopene 530, Betanin Riboflavin 445, Riboflavin 5I-monophosphate sodium salt 441, Erythrosin B sodium salt, teas.

22. The method of claim 15, further comprising the steps of:
d) stopping the irradiation; and
e) repeating steps c) and d) as necessary.

* * * * *